United States Patent
Thornton et al.

(10) Patent No.: US 10,220,156 B2
(45) Date of Patent: Mar. 5, 2019

(54) SINGLE USE INJECTOR

(71) Applicant: Adar MedTech, Inc., Englewood, CO (US)

(72) Inventors: Daniel William Thornton, Englewood, CO (US); Mark Christian Johnson, Phoenix, AZ (US)

(73) Assignee: ADAR MEDTECH, INC., Scottsdale, AZ (US)

( * ) Notice: Subject to any disclaimer, the term of this patent is extended or adjusted under 35 U.S.C. 154(b) by 637 days.

(21) Appl. No.: 14/634,537

(22) Filed: Feb. 27, 2015

(65) Prior Publication Data

US 2015/0165123 A1  Jun. 18, 2015

Related U.S. Application Data

(63) Continuation-in-part of application No. 14/052,167, filed on Oct. 11, 2013, now Pat. No. 9,265,889, which
(Continued)

(51) Int. Cl.
*A61M 5/32* (2006.01)
*A61M 5/28* (2006.01)
(Continued)

(52) U.S. Cl.
CPC .......... *A61M 5/3202* (2013.01); *A61M 5/282* (2013.01); *A61M 5/326* (2013.01);
(Continued)

(58) Field of Classification Search
CPC .... A61M 5/282; A61M 5/288; A61M 5/2466; A61M 5/24; A61M 5/2425;
(Continued)

(56) References Cited

U.S. PATENT DOCUMENTS 4,703,781 A * 11/1987 Meyer ..................... A61J 1/062
141/11
5,147,311 A * 9/1992 Pickhard ............... A61M 5/148
604/131
(Continued)

FOREIGN PATENT DOCUMENTS

DE 102014008610 A1 * 12/2015 .......... A61M 5/2466

*Primary Examiner* — Emily L Schmidt
*Assistant Examiner* — Alexandra Lalonde

(57) ABSTRACT

A single use injector is a disposable injection device that is specifically optimized for production using the blow fill seal (BFS) manufacturing process and includes various mechanisms that render the device inoperable and facilitate its safe disposal after use. The single use injector incorporates an ampoule aseptically filled with a medication that is coupled to a hermetically sealed component system. The hermetically sealed component system incorporates various mechanisms that are actuated during the use of the injection device. The injection device is encased in a removable overtube that prevents contamination. upon removal of the overtube, the injection device is activated, by compression of a needle cap that irreversible punctures the ampoule in order to inject the medication through a needle. The injection device additionally incorporates a shield that deploys over the needle following injection of the medication into a patient.

16 Claims, 11 Drawing Sheets

Related U.S. Application Data is a continuation-in-part of application No. 13/870,815, filed on Apr. 25, 2013, now abandoned.

(60) Provisional application No. 61/638,059, filed on Apr. 25, 2012.

(51) Int. Cl.

| | |
|---|---|
| A61M 5/50 | (2006.01) |
| B29L 31/00 | (2006.01) |
| B29C 49/04 | (2006.01) |
| A61M 5/31 | (2006.01) |
| A61M 5/00 | (2006.01) |

(52) U.S. Cl.
CPC ............. *A61M 5/002* (2013.01); *A61M 5/288* (2013.01); *A61M 5/3271* (2013.01); *A61M 5/50* (2013.01); *A61M 2005/312* (2013.01); *A61M 2005/3247* (2013.01); *B29C 49/04* (2013.01); *B29C 2791/006* (2013.01); *B29L 2031/7544* (2013.01)

(58) Field of Classification Search
CPC ........ A61M 35/003; A61M 2005/2474; A61M 5/32; A61M 5/3257; A61M 5/3202; A61M 5/326; A61M 5/002; A61M 5/3271; A61M 5/50; A61M 5/2429; A61M 5/2455; A61M 2005/3247; A61M 2005/3261; A61M 5/3272; A61M 5/3243; A61M 2005/3268; A61M 2005/3228; A61M 2005/3235; A61M 5/345; A61M 5/347; A61M 5/348; A61J 1/06

See application file for complete search history.

(56) References Cited

U.S. PATENT DOCUMENTS

| | | | | |
|---|---|---|---|---|
| 5,415,645 | A * | 5/1995 | Friend | A61M 5/326 604/110 |
| 5,575,769 | A * | 11/1996 | Vaillancourt | A61M 39/045 604/86 |
| 6,123,688 | A * | 9/2000 | Botich | A61M 5/24 604/110 |
| 2005/0148932 | A1* | 7/2005 | Rimlinger | A61M 5/31501 604/110 |
| 2005/0171485 | A1* | 8/2005 | Larsen | A61M 5/326 604/198 |
| 2006/0229583 | A1* | 10/2006 | Nagao | A61J 1/067 604/403 |
| 2010/0234811 | A1* | 9/2010 | Schubert | A61M 5/326 604/198 |
| 2013/0231614 | A1* | 9/2013 | Cross | A61M 5/3243 604/198 |
| 2015/0073352 | A1* | 3/2015 | Finke | A61L 2/0035 604/189 |
| 2017/0128676 | A1* | 5/2017 | Spallek | A61M 5/347 |

* cited by examiner

SINGLE USE INJECTOR

The current application is a continuation in part of U.S. Utility patent application Ser. No. 14/052,167 filed Oct. 11, 2013, which is a continuation in part of U.S. Utility patent application Ser. No. 13/870,815 filed Apr. 25, 2013, which claims benefit of provisional 61/638,059 filed Apr. 25, 2012.

FIELD OF THE INVENTION

The present invention relates generally to a single use syringe, more specifically to a prefilled single use medical injection device that is particularly designed for the Blow Fill Seal manufacturing process.

BACKGROUND OF THE INVENTION

There exists a plurality of the hypodermic syringe type injection device available for use. The vast majority of the devices are derivative of French physician Charles Pravaz' well-known design. The design consists of a cylinder body, a piston, and a hypodermic needle. This design works very well for introducing and extracting fluids from patients, and has been adapted recently as a prefilled delivery method made suitable by following specific pre-determined safety protocols that add significant cost to the infusion equation.

Prefilled medical injection devices provide health care workers with a more efficient way to administer medications. The ubiquitous hypodermic syringe has seen a multitude of incremental advancements and improvements over the years in order to deal with the myriad of problems hypodermic syringes present in its manufacture, distribution, storage and use. Many of these advancements are unique to the problems relating to the prefilled syringe, which creates many new challenges because of the prefilled format. For example, prefilled hypodermic syringes face problems relating to chemical interactions with silicone, a common lubricant that allows the plunger to move down the cylinder, as well as adhesives, rubber, and tungsten. Further, transportation presents additional problems relating to atmospheric changes, creating a potential for pressure increases inside the cylinder body causing the device to extrude medication, wasting medication, while decreases cause the device to suction up outside air, which increases the risk of contamination. Many other problems exist in their use, such as the accidental removal or dislodgement of the plunger, as well as the potential for needle stick injury depending upon the type of needle used. This has been a problem to many health care professionals and has forced them to switch back to the vial syringe method for delivering vaccinations.

Although, there are multitudes of prior arts that incorporate solutions to the above problem the majority of them still carry a major disadvantage. The majority of injection devices require that the device be uncapped and recapped to avoid sticking others with a contaminated needle. The requirement to recap a syringe has created a major risk factor for healthcare workers, accidentally pricking themselves with a soiled needle.

It is therefore an object of the present invention to introduce a device that is prefilled with medication, adjusts to changes in ambient temperature and pressure, while providing a risk reducing mechanism to inject patients. Additionally the invention is designed for a mass production method (Blow-Fill-Seal method) that minimizes the risk of contamination. Blow-Fill-Seal has numerous requirements and limitations and the ampoule and collar (insertion technology) have both been designed to be compatible with Blow-Fill-Seal manufacturing.

BRIEF DESCRIPTIONS OF THE DRAWINGS

DETAIL DESCRIPTIONS OF THE INVENTION

All illustrations of the drawings are for the purpose of describing selected versions of the present invention and are not intended to limit the scope of the present invention.

Figure 1:
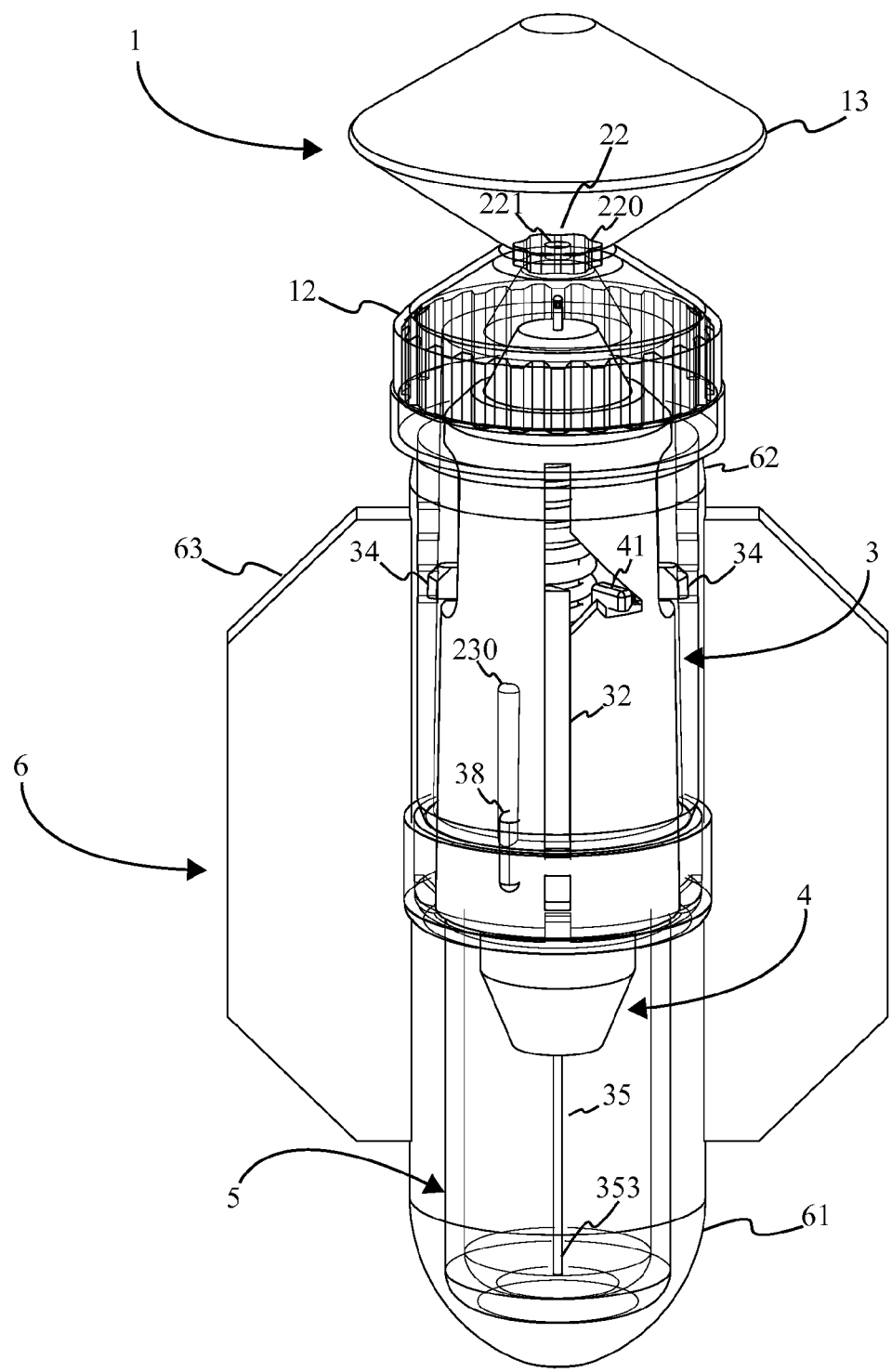
FIG. 1 is a perspective view displaying the single use injector in the initial configuration.
Figure 2:
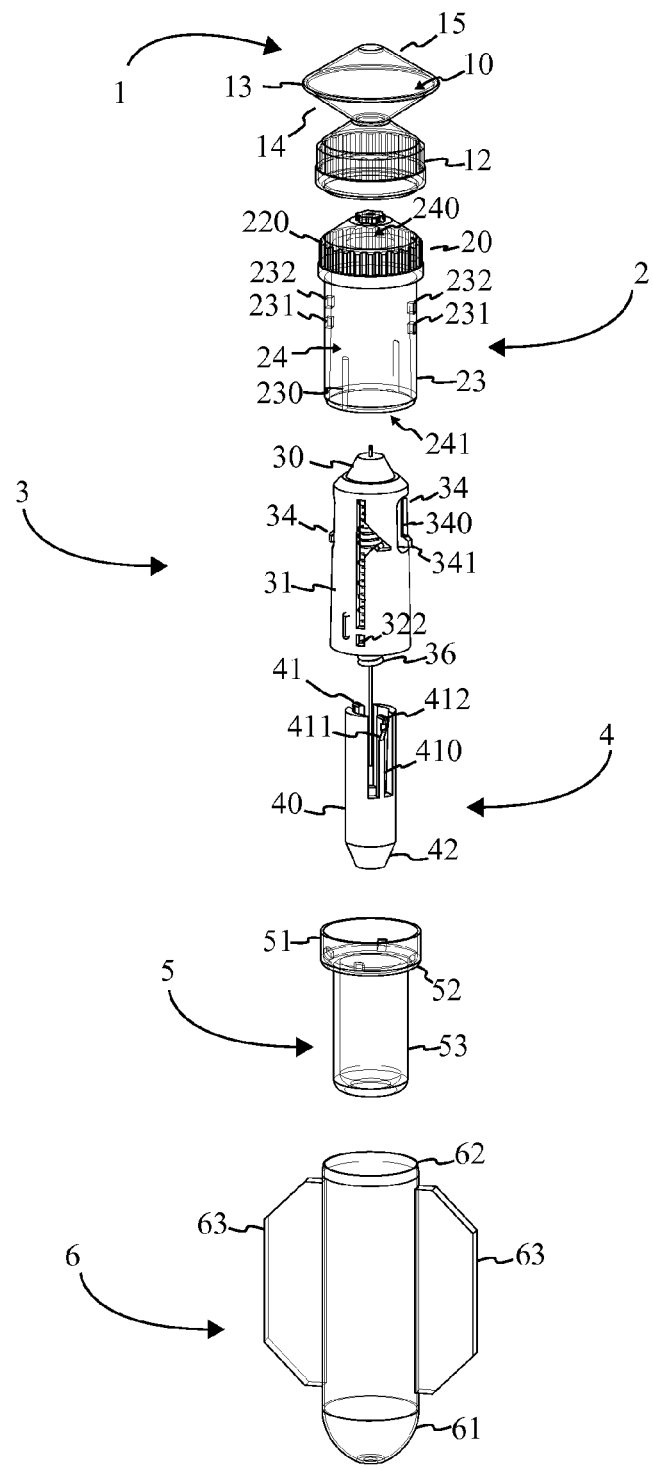
FIG. 2 is an expanded perspective view displaying the components of the single use injector in the initial configuration.
Figure 3:
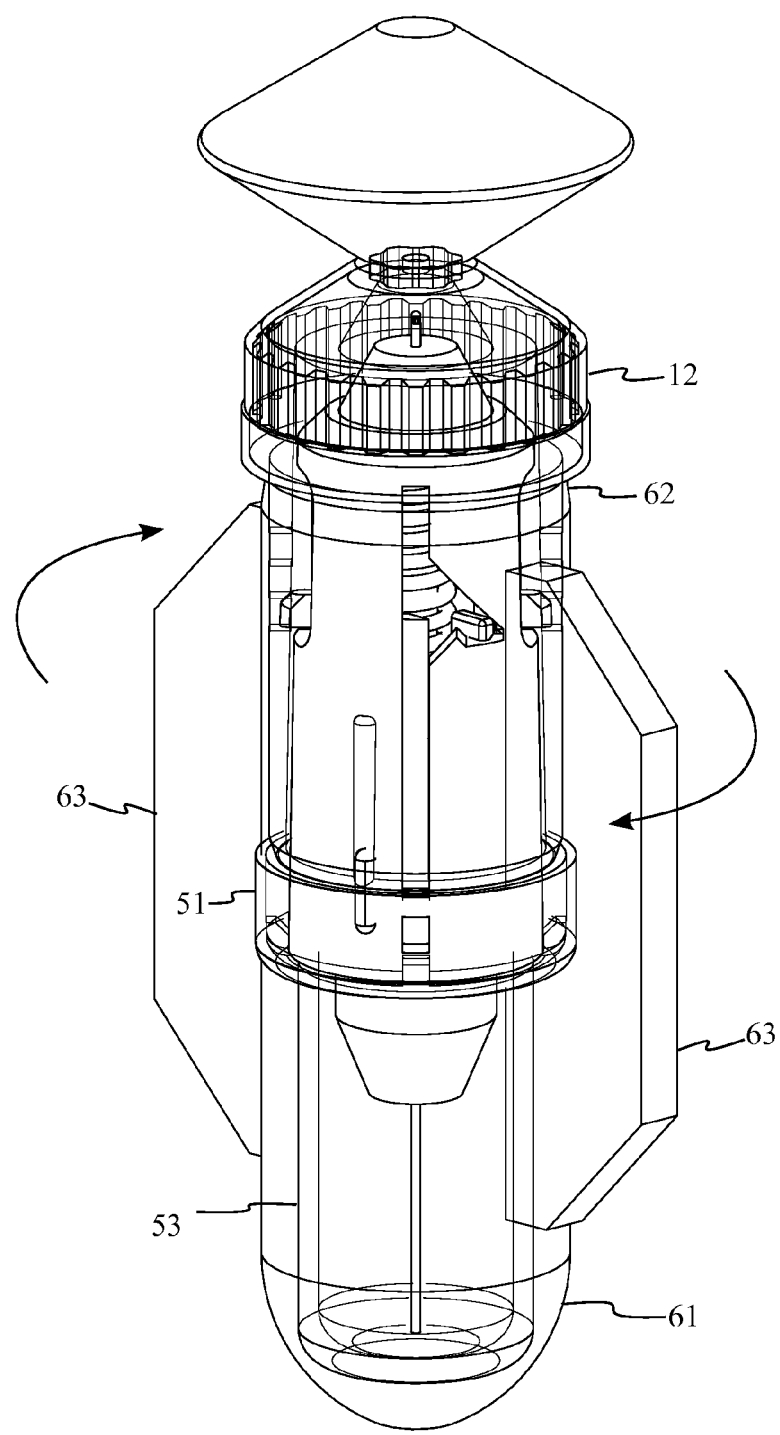
FIG. 3 is a perspective view displaying a transition stage of the single use injector where the overtube is being rotated to facilitate separation at the frangible features.
Figure 4:
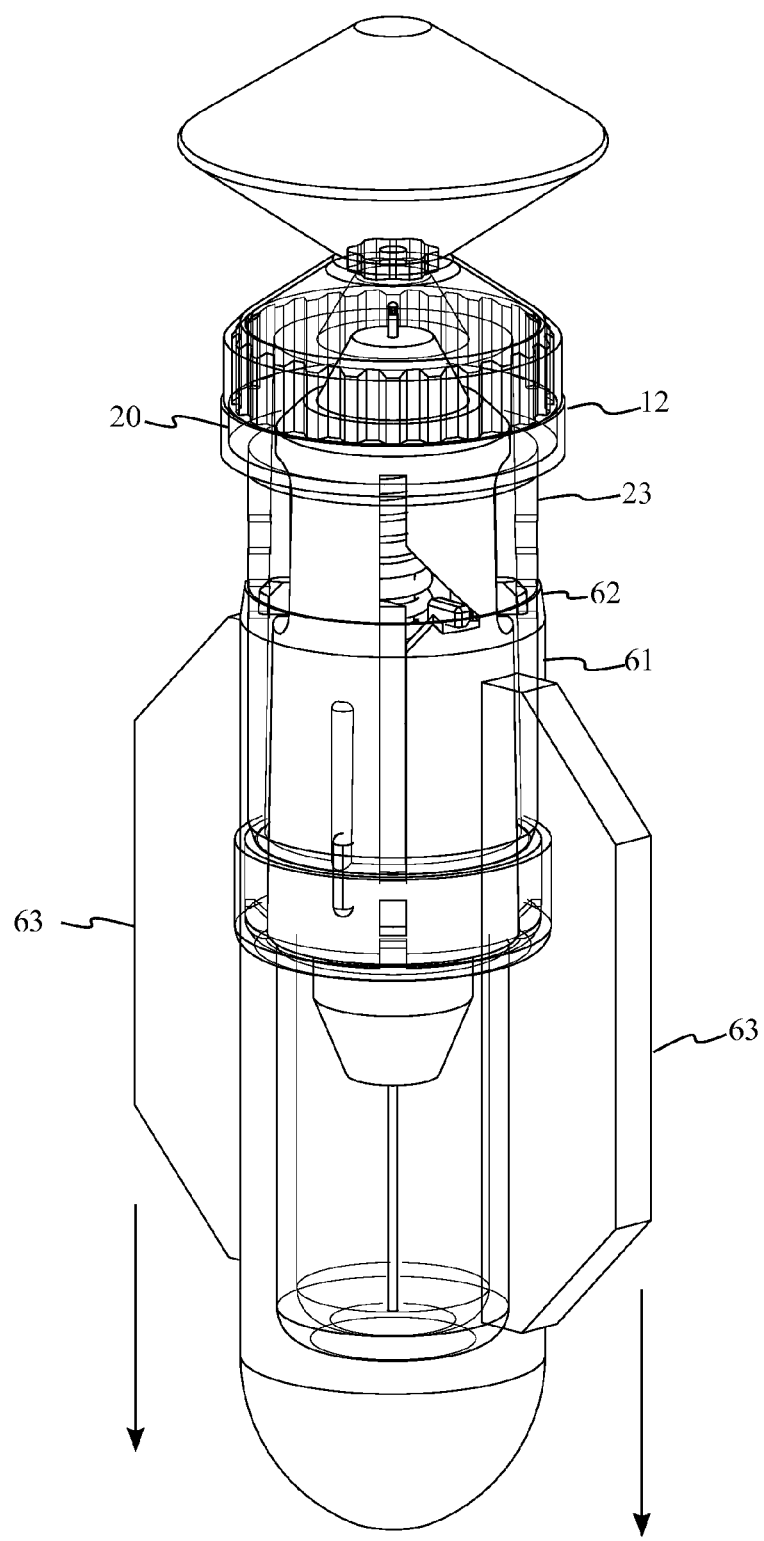
FIG. 4 is a perspective view displaying a transition stage of the single use injector where the overtube is being pulled off.
Figure 7:
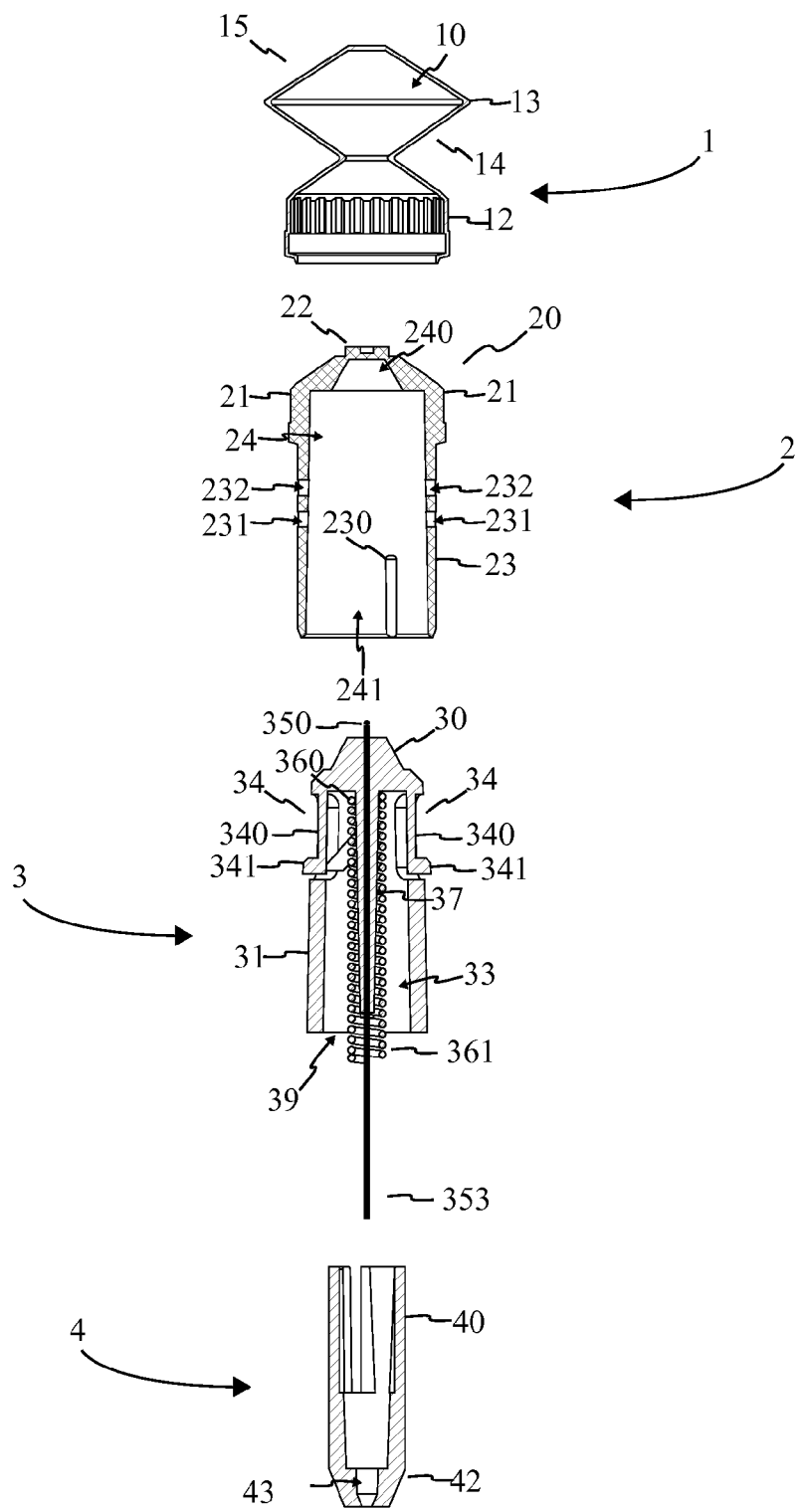
FIG. 7 is an expanded sectional view displaying the interior regions and the alignment of the components of the single use injector as per the activated configuration.

Referencing FIG. 1, FIG. 2, and FIG. 7, the single use injector is a disposable injection device that is specifically optimized for production using the blow fill seal (BFS) manufacturing process and includes various mechanisms that render the device inoperable and facilitate its safe disposal after use. The single use injector comprises an insert body 2, a needle assembly 3, a shield assembly 4, a needle cap 5, an ampoule 1 and an overtube 6. The ampoule 1 is the liquid filled volume created using the BFS process. The ampoule 1 is attached to the insert body 2 through a parison layer. The insert body 2 is rigid in construction and enables interactions between the needle assembly 3 and the ampoule 1. The needle assembly 3 penetrates the ampoule 1 through the insert body 2 and provides a conduit for injecting the contents of the ampoule 1 into a patient. The shield assembly 4 is a safety component that automatically extends over the needle 35 of the needle assembly 3 after use. The needle cap 5 protects the needle 35 of the needle assembly 3 from contamination. The needle cap 5 additionally serves as the means of activating the single use injector as compression of the needle cap 5 towards the ampoule 1 moves the needle assembly 3 into the activated position puncturing the ampoule 1. The overtube 6 is a removable packaging that is formed over the insert body 2 and the needle cap 5 during the BFS process. The overtube 6 separates from the single use injector at a frangible feature 62 positioned adjacent to the ampoule 1 on the insert body 2.

Referencing FIGS. 3-6 and FIGS. 8-10, the single use injector incorporates several mechanisms that render the injector inoperable as well as facilitate its safe disposal after use. The mechanisms involve interactions between two or more components that result in the alteration of the placement or configuration of at least one component. In the current embodiment of the present invention, the single use injector comprises three main configurations, an initial configuration, an activated configuration, and a deactivated configuration. The initial configuration is characterized by the overtube 6 covering the insert body 2 and the needle cap 5 with the parison layer 12 of the ampoule 1 being coupled to the parison layer 61 of the overtube 6 at the frangible features 62. The activated configuration is characterized by the absences of the overtube 6 and the needle cap 5, and with the needle assembly 3 puncturing the prefilled chamber 10 of the ampoule 1. The deactivated configuration is characterized by the volume of the prefilled chamber 10 being emptied and the ampoule 1 being in a fully compressed state while the shield assembly 4 being deployed and fully shrouding the needle 35. It should be noted that each configuration precedes or follows an interaction by a user that occurs as a result of operating the single use injector.

Referencing FIG. 2 and FIG. 5-7, in the current embodiment of the present invention, the insert body 2 provides an engagement point for the ampoule 1 and the needle assembly 3. The insert body 2 is cylindrically shaped and comprises an upper section 20, a cylindrical wall 23, and an inner chamber 24. The inner chamber 24 is the hollow interior of the insert body 2 that is accessible through a chamber opening 241. The cylindrical wall 23 surrounds the inner chamber 24 and comprises various features for engaging the needle assembly 3. The upper section 20 is positioned opposite the chamber opening 241 across the cylindrical wall 23 and serves as a mounting point for the ampoule 1. The upper section 20 is pierced by the needle assembly 3 in order to reach the ampoule 1.

Referencing FIG. 2 and FIG. 5-7, upper section 20 is particularly formed to interact with the ampoule 1 and the needle assembly 3. The upper section 20 is positioned generally perpendicular to the cylindrical wall 23. The upper section 20 of the insert body 2 comprises knurl features 21 and a collar 22. The knurl features 21 of the upper section 20 are an array of ridges positioned on the perimeter edge of the upper section 20 where it becomes coincident with the cylindrical wall 23. The knurl features 21 provide additional surface area to upper section 20 that improves the attachment and retention of the ampoule 1 to the upper section 20. The collar 22 is a protruding feature that extends centrally from the upper section 20 towards the ampoule 1. In the current embodiment of the present invention, the upper section 20 tappers towards the collar 22. The collar 22 comprises knurl features that are perimetrically positioned around the exposed portion of collar 22 on the upper section 20. The knurl features 220 of the collar 22 facilitate attachment and improve retention of the ampoule 1. The collar 22 additionally comprises a guide shaft 221 and a septum 222. The guide shaft 221 is a hollow shaft that traverses centrally through the upper section 20. The septum 222 functions as a barrier between the guide shaft 221 and the inner chamber 24. The septum 222 is pierced by the needle 35 of the needle assembly 3 in order to puncture the ampoule 1. The positioning of the guide shaft 221 to the needle assembly 3 is provided as a means of guiding the needle 35 after it pierces through the septum 222. It should be noted that the diameter of the guide shaft 221 is only slightly larger than that of the needle 35, in order to ensure that the walls of the guide shaft 221 are able to orient the needle 35 effectively.

Referencing FIG. 2 and FIG. 5-7, the cylindrical wall 23 surrounds the inner chamber 24 and is bounded by the chamber opening 241 and the upper section 20. The cylindrical wall 23 interacts with the needle assembly 3 during the transition between the initial configuration and the activated configuration. The cylindrical wall 23 comprises a first pair of slots 231, a second pair of slots 232, and a pair of alignment channels 230.

Referencing FIG. 2 and FIG. 5-7, the first pair of slots 231 and the second pair of slots 232 function as part of a locking mechanism that prevents the needle assembly 3 from returning to the initial configuration. The first pair of slots 231 and the second pair of slots 232 are aligned on the cylindrical wall 23 to engage a pair of snapping hooks 34 of the needle assembly 3 as the needle assembly 3 moves towards the upper section 20. Each snapping hook 34 of the pair of snapping hooks 34 is positioned oppositely on the needle assembly 3. As such each slot of the first pair of slots 231 is positioned on the cylindrical wall 23 across the inner chamber 24, while each slot of the second pair of slots 232 is positioned on the cylindrical wall 23 across the inner chamber 24. The first pair of slots 231 and the second pair of slots 232 are associated with a particular configuration of the single use injector. The first pair of slots 231 is associated with the initial configuration while the second pair of slots 232 is associated with the activated configuration. As a result of the second pair of slots 232 association with the activated configuration, the second pair of slots 232 are positioned adjacent the upper section 20, relative to the first pair of slots 231. Furthermore, the interior surface of the cylindrical wall 23 is angled towards the upper section 20 resulting in a narrowing of the inner chamber 24 which improves engagement with the second pair of slots 232.

Referencing FIG. 1, FIG. 2 and FIG. 5-7, the pair of alignment channels 230 are recessed features positioned on the portion of the cylindrical wall 23 coincident with the inner chamber 24, adjacent to the chamber opening 241. The pair of alignment channels 230 are complementary features to a pair of guides 38 positioned on the lateral wall 31 of the needle assembly 3. The pair of guides 38 are semicircular protrusions oppositely positioned on the exterior surface of the needle assembly 3 adjacent to the cavity opening 39 of the needle assembly 3. Each guide of the pair of guides 38 is found coincident within an alignment channel 230 of the pair of alignment channels 230. The positioning of each guide with an alignment channel 230 restricts the movement of the needle assembly 3 within the inner chamber 24 to follow along the path of the alignment channel 230. The engagement between the pair of alignment channels 230 and the pair of guides 38 prevents unwanted lateral rotation of the needle assembly 3 as it transitions from the initial configuration to the activated configuration.

Referencing FIG. 2 and FIG. 5-7, the inner chamber 24 of the insert body 2 receives the needle assembly 3. The needle assembly 3 is contained within the inner chamber 24 and the engagement between the cylindrical wall 23 and the needle assembly 3 restrict its movement while transitioning between the initial and activated configuration. Interactions between the inner chamber 24 and the needle assembly 3 occur through a conical shaped needle mount 30 of the needle assembly 3 and a conical shaped cavity 240 within the inner chamber 24. The conical shaped cavity 240 is a concave feature that is positioned within the inner chamber 24 and coincident with the upper section 20. The conical shaped cavity 240 is positioned centrally to the upper section 20 within the inner chamber 24. As a result of the positioning, the conical shaped cavity 240 is centrally aligned with the septum 222 of the collar 22. The walls of the conical shaped cavity 240 narrow towards the upper section 20. The narrowing walls serve to guide the conical shaped needle mount 30 towards the center in order to penetrate the septum 222. The conical shaped cavity 240 is particularly formed to receive the conical shaped needle mount 30 of the needle assembly 3 during the transition from the initial configuration to the activated configuration. The conical shaped cavity 240 is slightly smaller in diameter than the conical shaped needle mount 30. The disparity in size causes the conical shaped needle mount 30 to wedge itself into the conical shaped cavity 240 forming a gasket-like seal when the needle 35 transitions in the activated configuration.

Referencing FIG. 1, FIG. 2, and FIG. 5-7, the needle assembly 3 is particularly shaped to interact with the insert body 2, the shield assembly 4, and the ampoule 1. The needle assembly 3 is cylindrically shaped, similar to the insert body 2 and the shield assembly 4, but comprises various laterally positioned features to engage both the inset body and the shield assembly 4. The needle assembly 3 comprises a lateral wall 31, a cavity 33, a conical shaped needle mount 30, a spring 36, and a needle 35. The lateral wall 31 surrounds the cavity 33 of the needle assembly 3 and serves as the engagement point for various interacting features. The lateral wall 31 is bounded by the conical shaped needle mount 30 and the cavity 33 opening. The cavity 33 is the interior region of the needle assembly 3 that is surrounded by the lateral wall 31. The spring 36 is contained within the cavity 33 and compressed by the shield assembly 4. The shield assembly 4 is positioned within the cavity 33 of the needle assembly 3, retained by a pair of engagement features interacting with the lateral wall 31. The conical shaped needle mount 30 is positioned on the exterior of the needle assembly 3 adjacent the conical shaped cavity 240 of the insert body 2. The needle 35 is the conduit that is centrally poisoned on the needle assembly 3 traversing the conical shaped needle mount 30 and through the cavity 33. The needle 35 punctures the ampoule 1 enabling the contents of the prefilled chamber 10 to be injected into a patient.

Referencing FIG. 2 and FIG. 5-7, the conical shaped needle mount 30 is positioned on the exterior portion of the needle assembly 3. When viewed laterally, the conical shaped needle mount 30 has a trapezoidal profile. The conical shaped needle mount 30 is centrally traversed by the needle 35. The puncturing end 350 of the needle 35 centrally protrudes from the conical shaped needle mount 30 towards the conical shaped cavity 240. The length of the puncturing end 350 of the needle 35 is sufficient to penetrate the septum 222, traverse the guide shaft 221, and pierce a membrane 11 of the prefilled chamber 10. The conical shaped needle mount 30 becomes coincident with the conical shaped cavity 240. The conical shaped needle mount 30 has a slightly larger diameter than conical shaped cavity 240. The larger diameter allows the conical shaped needle mount 30 wedge into the conical shaped cavity 240 when the needle assembly 3 is being positioned into the activated configuration.

Referencing FIG. 1, FIG. 2 and FIG. 5-7, the lateral wall 31 of the needle assembly 3 is positioned surrounding the cavity 33 and the needle 35. The lateral wall 31 bounded by the conical shaped needle mount 30 and the cavity 33 opening. The lateral wall 31 comprises several features that directly engage the insert body 2 and the shield assembly 4. These features comprise a pair of snapping hooks 34, needle shield activation channels 32, and a pair of guides 38. The pair of snapping hooks 34 are the interacting features that engage the first pair of slots 231 and the second pair of slots 232. Each snapping hook 34 of the pair of snapping hooks 34 are oppositely positioned on the exterior portion of the lateral wall 31. The positioning of each snapping hook 34 permits a coincident alignment with the first pair of slots 231 and the second pair of slots 232.

Figure 5:
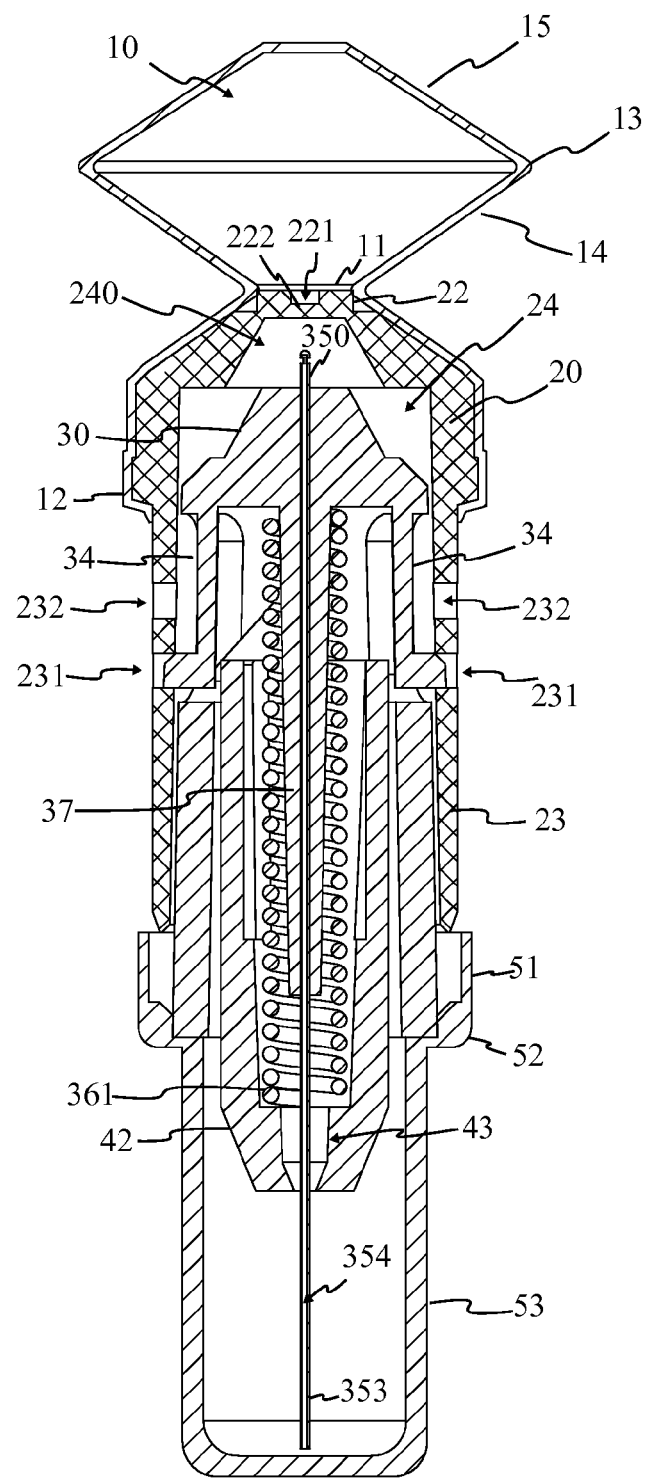
FIG. 5 is a sectional view displaying the needle assembly coupled to the first pair of slots as per the initial configuration.
Figure 6:
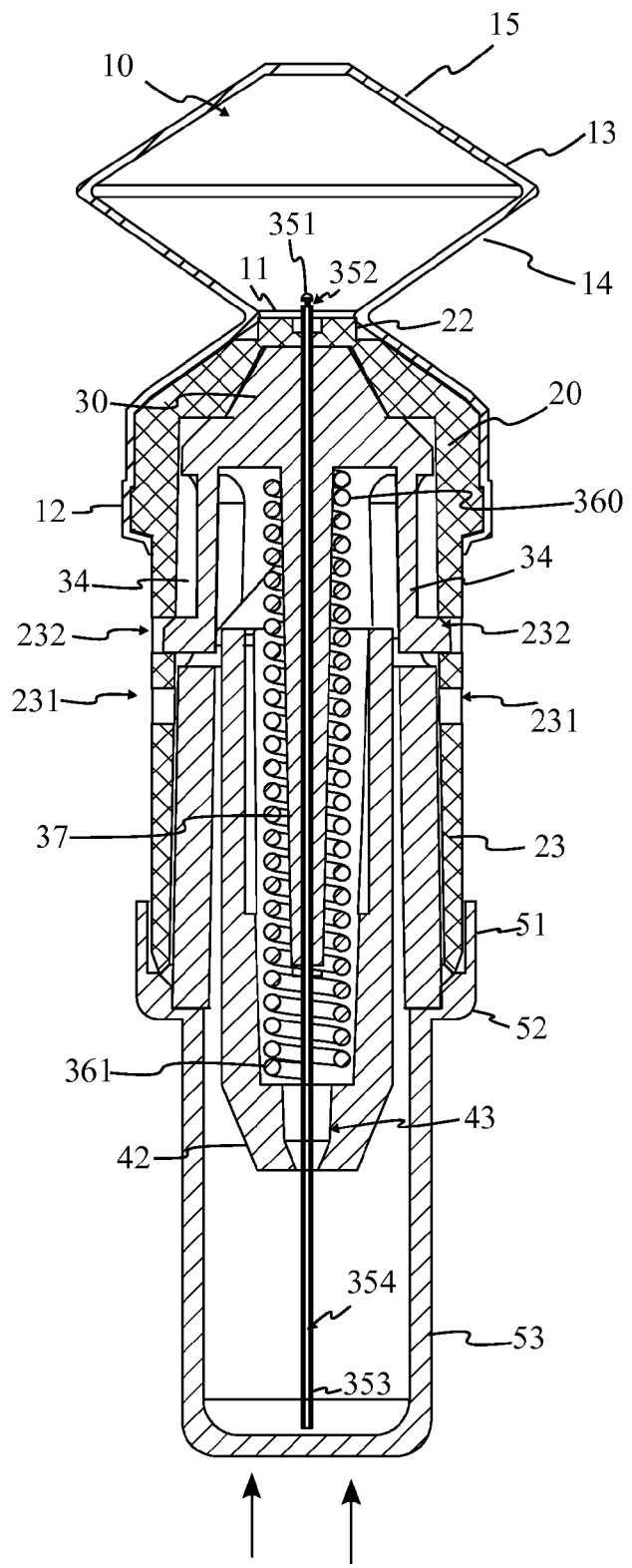
FIG. 6 is a sectional view displaying the needle assembly coupled to the second pair of slots as per the activated configuration.

Referencing FIG. 5-7, each snapping hook 34 of the pair of snapping hooks 34 comprises a flexible arm 340 and a stud 341. The flexible arm 340 and the stud 341 function as a pawl for disengaging and engaging the first pair of slots 231 and the second pair of slots 232 in one direction. The flexible arm 340 is connected to the lateral wall 31, while the stud 341 is terminally positioned on the opposite end of the flexible arm 340 relative to the connection with the lateral wall 31. The positioning of the stud 341 relative to the connection enables the stud 341 to compress and pivot through as a result of the elastic construction of the flexible arm 340.

Referencing FIG. 5, FIG. 6, and FIG. 7, during the initial configuration, the stud 341 is positioned within a slot of the first slot. When the needle assembly 3 begins to move towards the upper section 20 during the transition stage, the stud 341 disengages from the slot of the first pair of slots 231 and becomes coincident with the interior surface of the cylindrical wall 23 as a result of the compression of the flexible arm 340. The compression of the flexible arm 340 allows the stud 341 to traverse the space between the first pair of slots 231 and the second pair of slots 232. When the stud 341 aligns with a slot of the second pair of slots 232, the flexible arm 340 relaxes and moves the stud 341 into a secure engagement with the second pair of slots 232.

It should be noted that the stud 341 incorporates sloped feature that allow for facilitated disengagement from the slot of the first pair of slots 231 while moving towards the upper section 20 while incorporating feature that prevent disengagement in the reverse direction. Additionally it should be noted that the stud 341 and the flexible arm 340 compress inwardly towards the cavity 33 of the needle assembly 3 while moving towards the upper section 20.

Referencing FIG. 1 and FIG. 2, the pair of guides 38 are oppositely positioned on the exterior portion of the lateral wall 31 adjacent to the cavity 33 opening. Each guide of the pair of guides 38 becomes coincident with an alignment channel 230 of the pair of alignment channels 230 on the interior surface of the cylindrical wall 23. The coincident engagement between each guide and an alignment channel 230 of the pair of alignment channels 230 prevents the needle assembly 3 from rotating while moving into the activated configuration.

Referencing FIG. 2 and FIG. 7-10, the needle shield activation channels 32 interact with activation tabs 41 of the shield assembly 4 in order to deploy the shield assembly 4 over the needle 35. The needle shield activation channels 32 guide the shield assembly 4 from its initial position, retained within the cavity 33 of the needle assembly 3, and transitions it to a deployed position in the deactivated configuration, shrouding the needle 35. The needle shield activation channels 32 comprise a first path 320, a second path 321, and an obstructing feature 323. The first path 320 and the second path 321 are excised from the lateral wall 31. The second path 321 is oriented from conical shaped needle mount 30 towards the cavity 33 opening. The first path 320 intersects the second path 321 proximal to the conical shaped needle mount 30. The intersect of the first path 320 and the second path 321 form an acute angle with the opening facing the towards the cavity 33 opening. The positioning of the first path 320 relative to the second path 321 is provided to direct the activation tab 41 towards the second path 321 during compression of the shield assembly 4. The obstructing feature 323 is positioned in the angle opening formed by the first path 320 and the second path 321. The obstructing feature 323 prevents rotation of the shield assembly 4 from repositioning the activation tab 41 into the second path 321. The obstructing feature 323 retains an activation tab 41 within the first path 320 until the shield assembly 4 is compressed against a patient.

Figure 8:
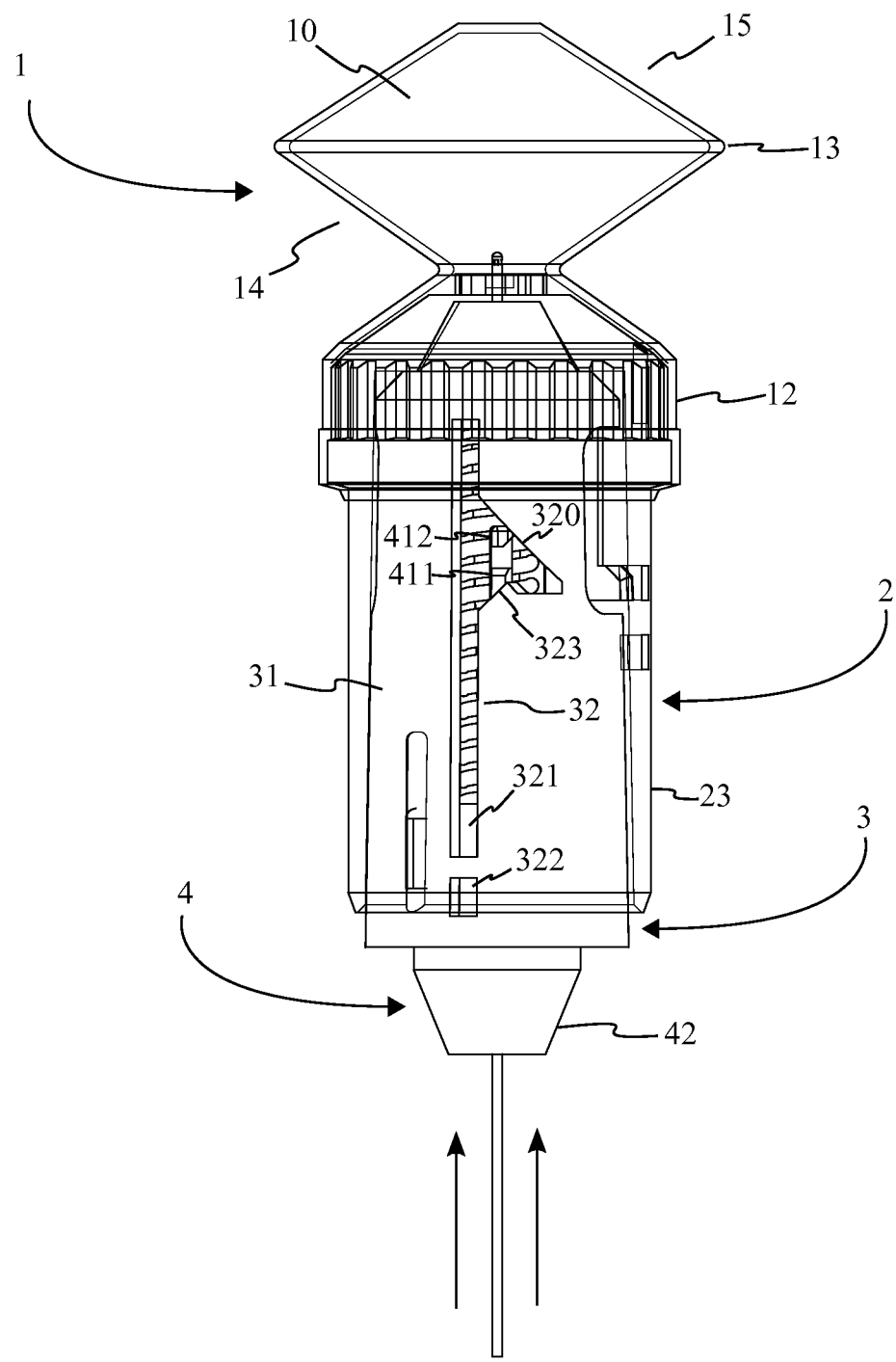
FIG. 8 is a lateral view displaying the second engagement feature following the first path of the needle shield activation channel.
Figure 9:
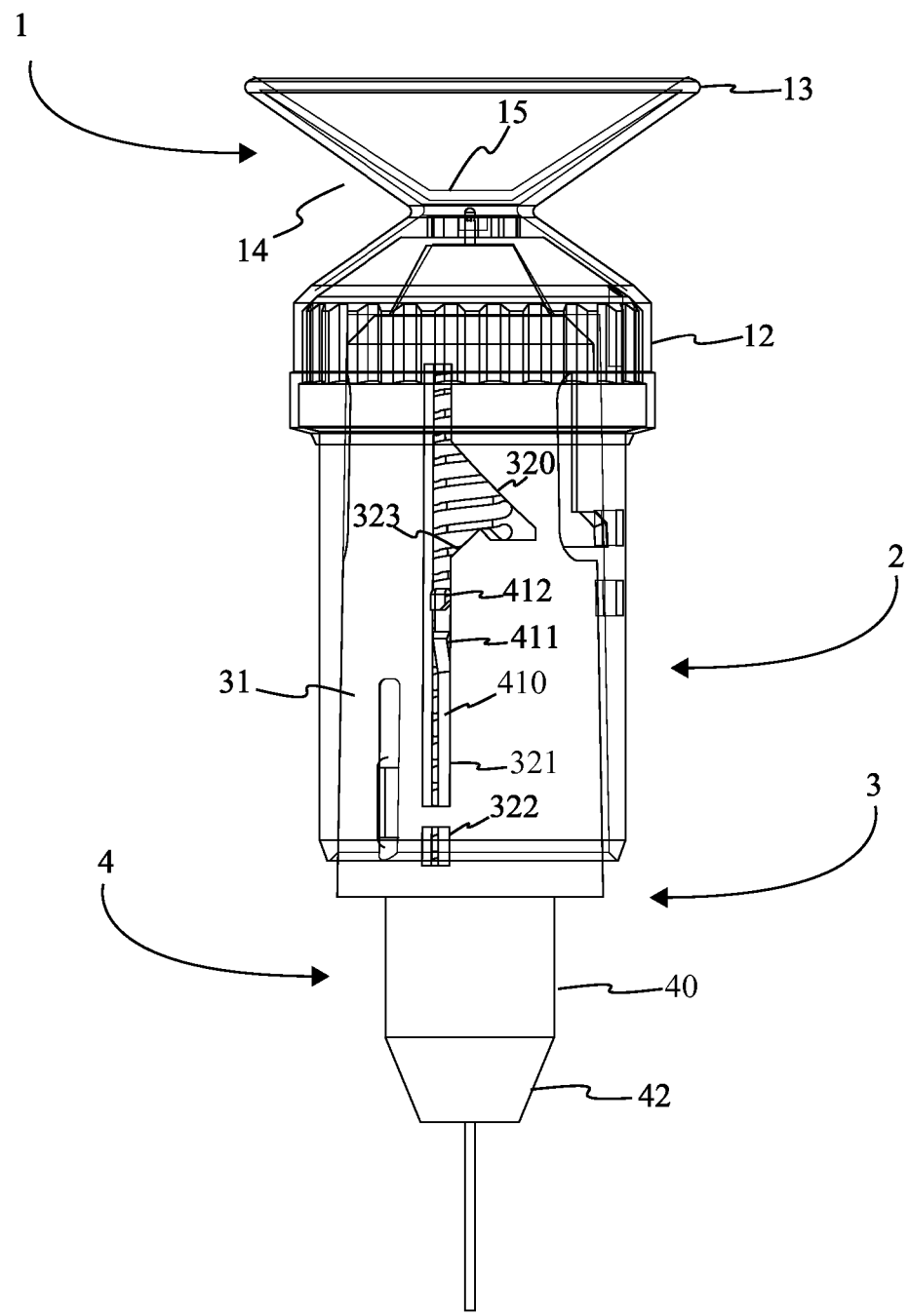
FIG. 9 is lateral view displaying the activation tab traversing the second path during the deployment of the shield assembly over the needle.
Figure 10:
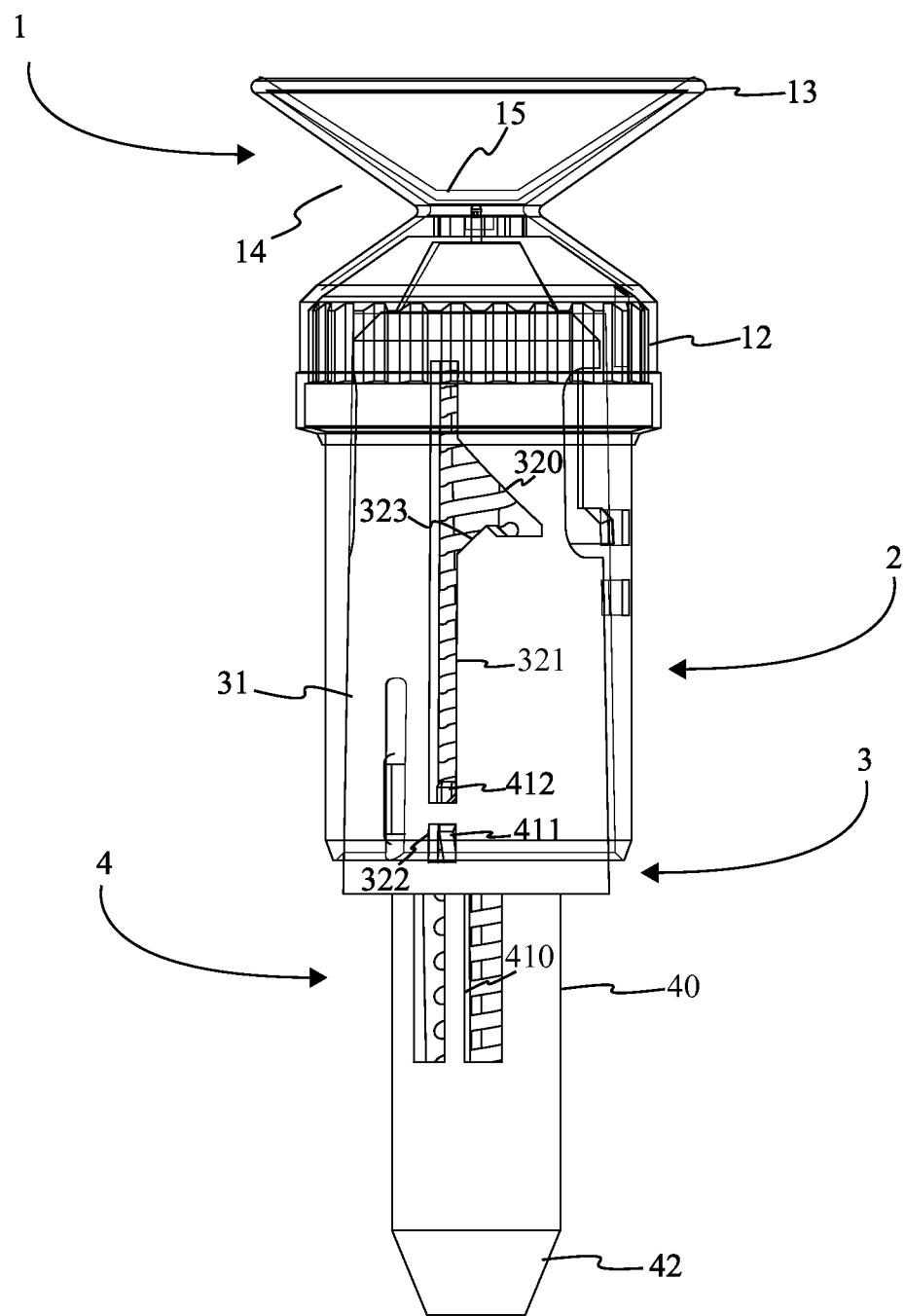
FIG. 10 is a lateral view displaying the shield assembly shrouding the needle and the activation tabs engaged to the locking mount, as per the deactivated configuration.
Figure 11:
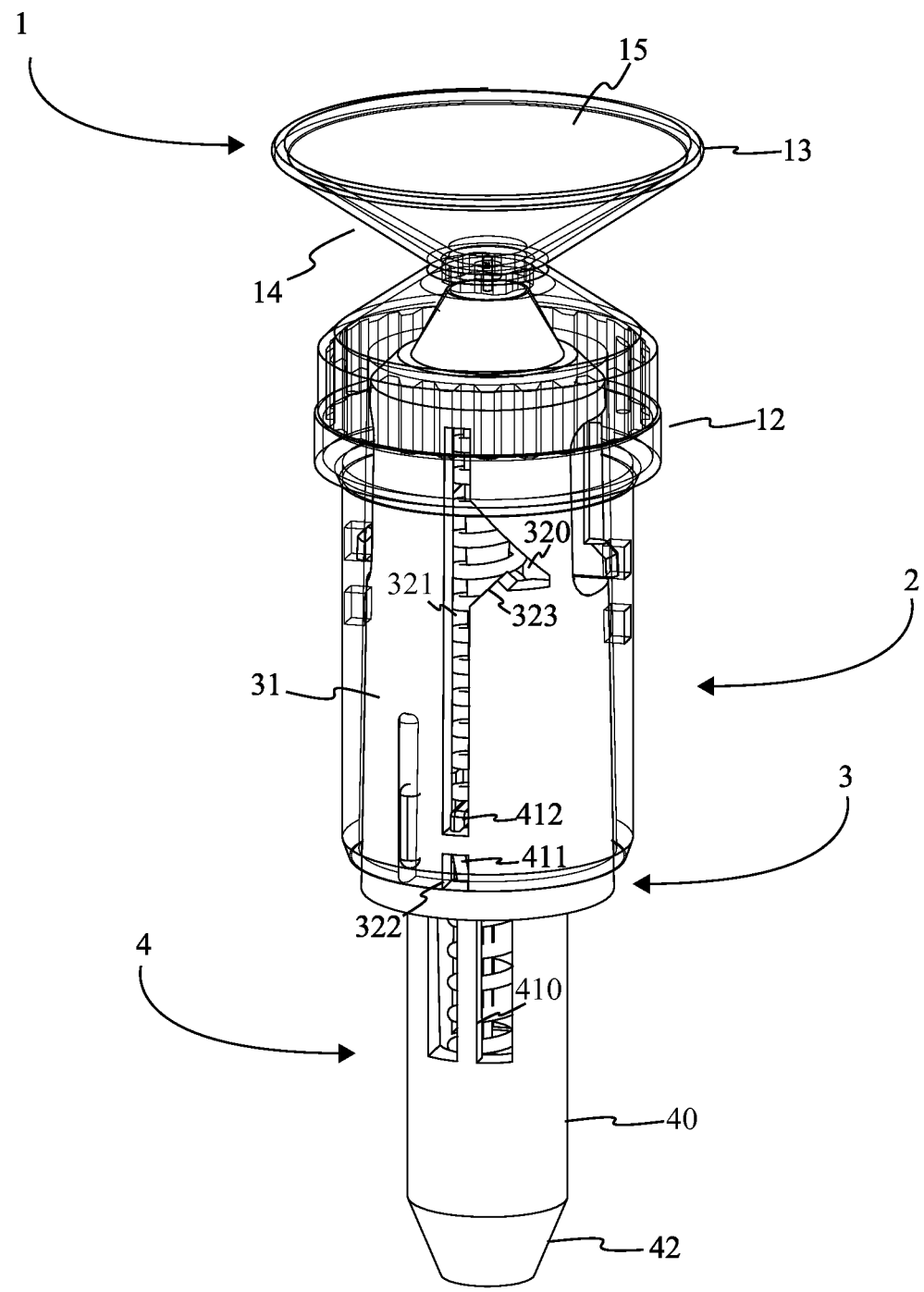
FIG. 11 is a perspective view displaying the single use injector is the deactivated configuration.

Referencing FIG. 2 and FIG. 8, the compression of the shield assembly 4 causes an activation tab 41 to travel along the first path 320 until. The activation tab 41 continues traveling along the first path 320 until the reaching the intersect point of the first path 320 and the second path 321. When that activation tab 41 is coincident with the second path 321, the spring 36 is able to extend the shield assembly 4 the length of the second path 321, until the activation tab 41 becomes coincident with a locking mount 322 of the second path 321. The locking mount 322 is positioned proximal to the cavity opening 39 of the second path 321 and securely engages the activation tab 41. The engagement between the activation tab 41 and the locking mount 322 prevents the shield assembly 4 from returning back to its position in the activated configuration.

Referencing FIG. 7, the cavity 33 is surrounded by the lateral wall 31 and contains the shield assembly 4 and the spring 36 during the activated configuration. The cavity 33 is accessible through a cavity opening 39 positioned perpendicular to the lateral wall 31 opposite the positioning of the conical shaped needle mount 30. The shield assembly 4 traverse into the cavity 33 through cavity opening 39 and is retained within the cavity 33 by the engagements with the lateral wall 31 through the needle shield activation channels 32. The cavity 33 houses the spring 36 that is compressed by the shield assembly 4. Within the cavity 33, a tapered spring mount 37 is positioned centrally through the cavity 33 with the mounting point found within the cavity 33 opposite the conical shaped needle mount 30. The tapered spring mount 37 is centrally traversed by the needle 35 and is sleeved by the spring 36. The tapered spring mount 37 is a long cone shaped rigid body that prevents the spring 36 from buckling. The spring 36 is compressed by the shield assembly 4 within the cavity 33. The spring 36 comprises a first spring end 360 and a second spring end 361 end. The first spring end 360 sleeves the tapered spring mount 37 within the cavity 33 while the second spring end 361 end is retained against a spring mount 42 of the shield assembly 4.

Referencing FIG. 1, FIG. 2, and FIG. 7, the needle 35 is centrally positioned through the needle assembly 3 and traverses the conical shaped needle mount 30 and the tapered spring mount 37. The needle 35 is used to pierce the ampoule 1 and transport the fluid contents of the ampoule 1 into a patient. The needle 35 comprises a puncturing end 350, an injection end 353, and a fluid conduit 354. The puncturing end 350 of the needle 35 is the visible portion of the needle 35 that extends from the conical shaped needle mount 30. The puncturing end 350 of the needle 35 pierces the septum 222 and traverses the guide shaft 221 before puncturing the membrane 11 of the ampoule 1. In an embodiment of the invention, the puncturing end 350 of the needle 35 comprises a rounded tip 351 and conduit opening 352. The rounded tip 351 is terminally positioned on the puncturing end 350 and facilitates the piercing of the septum 222. The rounded tip 351 additionally reduces the risk of dislodged shards created from piercing the septum 222 from obstructing the fluid conduit 354. The conduit opening 352 is positioned on the puncturing end 350 of the needle 35 adjacent to the rounded tip 351. The conduit opening 352 provides a passage for the fluid conduit 354. The conduit opening 352 is particularly formed for use with the rounded tip 351. After the puncturing end 350 traverses into the prefilled chamber 10 of the ampoule 1, the fluid conduit 354 is used to transport the fluids through the needle 35 and through the injection end 353.

Referencing FIG. 1, FIG. 2, and FIG. 7-10, the shield assembly 4 is a deployable safety feature that shrouds the needle 35 of the needle assembly 3 after use. The shield assembly 4 is engaged to the needle shield activation channels 32 on the lateral wall 31. The shield assembly 4 is retained within the cavity 33 during the initial configuration and the activated configuration. The shield assembly 4 is deployed by the engagement with the spring 36 after the shield assembly 4 is compressed during use. The shield assembly 4 comprises a barrel 40, activation tabs 41, and a spring mount 42. The barrel 40 of the shield assembly 4 is the generally cylindrical shaped body of the shield assembly 4. The barrel 40 sleeves the needle 35 and the spring 36. The second end of the spring 36 engages the spring mount 42 within the barrel 40. The spring mount 42 is an extension of the barrel 40 that comprises a needle passage 43. The needle passage 43 is the centrally positioned opening through which the needle 35 traverses the shield assembly 4. The needle passage 43 allows the shield assembly 4 to move over the needle 35 while being deployed into the deactivated configuration. The activation tabs 41 are positioned on the exterior of the barrel 40. The activations tabs are protrusions from the barrel 40 that laterally engage the needle shield activation channels 32 of the needle assembly 3. The activation tabs 41 comprise an elongated arm 410, a first engagement feature 411 and a second engagement feature 412. The elongated arm 410 runs coincident with the walls of the barrel 40. The elongated arm 410 is coupled to the barrel 40 adjacent to the spring mount 42. The first engagement feature 411 and the second engagement feature 412 are positioned on the distal portion of the elongated arm 410 opposite the spring mount 42. The elongated arm 410 and the positioning of the first engagement feature 411 and the second engagement feature 412 provide the activation tabs 41 with flexible characteristic allowing the positioning of the first engagement feature 411 and the second engagement feature 412 to compress. The second engagement feature 412 is the positioned further away from the spring mount 42 than the first engagement feature 411. The second engagement feature 412 is mostly perpendicular to the elongated arm 410. In the initial configuration and the activated configuration, the second engagement feature 412 is found coincident with the first path 320 of the needle shield activation channels 32 while the first engagement feature 411 is compressed against the interior surface of the lateral wall 31. The second engagement feature 412 is retained within the first path 320 by the obstructing feature 323. The obstructing features 323 prevent rotation of the shield assembly 4 from dislodging the second engagement feature 412 and aligning it with the second path 321. during the transition between the activated state and the deactivated state, compression of the shield assembly 4 near the spring mount 42 cause the second engagement features 412 to become coincident with the angled edge of the first path 320. The angled edge leads the second engagement feature 412 towards the second path 321. Compression of the shield assembly 4 compresses the spring 36. When the second engagement feature 412 becomes coincident with the second path 321 and compression to the shield assembly 4 is stopped, the spring 36 expands moving the second engagement feature 412 and the first engagement feature 411 along the second path 321 towards the cavity opening 39 of the needle assembly 3. The obstructing feature 323 is particularly formed to prevent the second engagement feature 412 from returning to its original location by have a slopped edge that would guide the second engagement feature 412 into the second path 321. The first engagement feature 411 is shaped similar to a wedge with the slopped edge oriented towards the spring mount 42. The first engagement feature 411 engages the locking mount 322 of the second path 321 by slightly compressing the elongated arm 410 and then snapping back into the locking mount 322. The transition of the activation tabs 41 along the needle shield activation channels 32 results in the shield assembly 4 extending over the injection end 353 of the needle 35.

Referencing FIG. 1-6, the needle cap 5 is a temporary enclosure for the needle 35. The needle cap 5 is coupled to the insert body 2 and positioned against the needle assembly 3 in the initial configuration. The needle cap 5 comprises a sleeve mount 51, a rim 52, and a protective cover 53. In the initial configuration, the needle cap 5 is covered by the parison layer 61 of the overtube 6. After the overtube 6 is removed the needle cap 5 protects the user handling the single use injector accidental sticking. The needle cap 5 additionally provides the user with an engageable surface to activate the single use injector. The sleeve mount 51 is positioned around the insert body 2 near the chamber opening 241. The sleeve mount 51 isn't tightly wrapped around the cylindrical wall 23, permitting movement. The rim 52 is positioned perpendicular to the sleeve mount 51 and is found coincident with the lateral wall 31 of the needle assembly 3 adjacent to the cavity 33 opening. The rim 52 is also perpendicular to the protective cover 53 that surrounds the needle 35 of the needle assembly 3. During the transition stage between the initial configuration and the activated configuration, the needle cap 5 pushed in towards the ampoule 1. The resulting action causes the rim 52 to compress against the lateral wall 31 of the needle assembly 3 pushing the puncturing end 350 of the needle 35 through the septum 222 and into the ampoule 1. Concurrently, the pair of snapping hooks 34 disengage from the pair of first slots and reengage with the pair of second slots, locking the needle assembly 3 in place. With the needle assembly 3 in the activated position, the needle cap 5 would be removed exposing the injection end 353 of the needle 35 for injection into a patient.

Referencing FIG. 1, FIG. 2, and FIG. 5-10, the ampoule 1 is the fluid filled container that is punctured by the needle 35. The ampoule 1 is positioned adjacent to the upper section 20 of the insert body 2. The ampoule 1 comprises a prefilled chamber 10, a parison layer, and a flexible body 13. The prefilled chamber 10 is the hermetically sealed volume that is surrounded by the flexible body 13. The prefilled chamber 10 is positioned against the collar 22 of the upper section 20 of the insert body 2. The parison layer 12 of the ampoule 1 is the same material that is used for the flexible body 13. The parison layer 12 of the ampoule 1 surrounds and engages the knurl features 21 of the upper section 20 and the collar 22 forming a secure engagement that retains the prefilled chamber 10 against the upper section 20.

Referencing FIG. 1, FIG. 2, and FIG. 5-10, the prefilled chamber 10 is aseptically formed during the BFS process. The flexible body 13 surrounds the prefilled chamber 10 and serves as the containing body. The material construction of the flexible body 13 provides it with an elasticity that serves as the means of compressing the volume of the prefilled chamber 10 in order to eject the contents out through the fluid conduit 354 of the needle 35. The prefilled chamber 10 comprises a medication and an inert gas. The medication is a solution that is injected into a patient through the needle 35. The walls of the flexible body 13 that interact with the contents of the prefilled chamber 10 are unlikely to interact or bleed chemicals into the medication overtime, due to the material construction of the prefilled chamber 10. The inert gas is used to fill any remaining headspace. The inert gas provides resistance to volume changes due to changes in pressure and temperature. It should be noted that the inert gas can be introduced into the prefilled chamber 10 after the medication is filled the chamber. The inert gas would then be used to replace any remaining voided space.

Referencing FIG. 1, FIG. 2, and FIG. 5-10, the prefilled chamber 10 is enclosed by the flexible body 13. A membrane 11 is positioned between the prefilled chamber 10 and the upper section 20 of the insert body 2. The membrane 11 seals the prefilled chamber 10 within the flexible body 13 and serves as the puncturing point for the prefilled chamber 10. During the transition stage between the initial configuration and the activated configuration, the membrane 11 is pierced by the puncturing end 350 of the needle 35. The puncturing end 350 of the needle 35 places the fluid conduit 354 in communication with the injection end 353. The prefilled chamber 10 and the membrane 11 are retained against the collar 22 through the engagement between the knurl features 220 of the collar 22 and the parison layer 12 of the ampoule 1. In an embodiment of the present invention, the membrane 11 is an adhesive membrane has an adhesive layer facing the surface of the collar 22. The adhesive membrane provides an additional means of securing the prefilled chamber 10 to the collar 22. The adhesive membrane is pierced by the puncturing end 350 of the needle 35.

Referencing FIG. 1, FIG. 2, and FIG. 5-10, the flexible body 13 that surrounds the prefilled chamber 10 is designed to fully eject the volume of the prefilled chamber 10 through the needle 35. The flexible body 13 accomplishes this through its particular shape. The flexible body 13 comprises a first section 14 and a second section 15. The first section 14 is shaped to taper towards the collar 22 and thus towards the puncturing end 350 of the needle 35 positioned within the prefilled chamber 10. The second section 15 is symmetrical to the first section 14 but opposite the wider section of the first section 14. The profile view of the flexible body 13 appears hexagonal in the initial configuration and the activated configuration. The particular shape of the flexible body 13 is provided as a means of ensuring compression of the flexible body 13 can eject the entire volume of the prefilled chamber 10 through the needle 35. During the injection stage that occurs following the activated configuration, the second section 15 of the flexible body 13 is depressed by causing an inversion of its shape towards the first section 14. The inversion of the second section 15 reduces the volume within the prefilled chamber 10 by forcing the contents to be expelled through the needle 35. When the second section 15 is fully inverted, the interior walls of the second section 15 are coincident with the interior walls of the first section 14. The volume within the prefilled chamber 10 is completely voided resulting in zero holdback space. By providing a construction that resulting zero holdback space, the flexible body 13 will be unable to be reused. With the contents of the prefilled chamber 10 emptied, the ampoule 1 is in the deactivated configuration. It should be noted that in the BFS manufacturing process, a narrowed closed off section, known as a neck, is formed when sealing off a filled container section, analogous to the ampoule, of a mold. While the neck feature is ubiquitous in the BFS manufacturing process is does create additional space within a fill container section that translates into a holdback space for a fluid. The preferred embodiment of the present invention positions the collar 22 within the formed neck of the ampoule 1 resulting in a "no-neck" design that eliminates holdback space.

In some embodiments of the present invention, it may be necessary for the present invention to have a neck due to manufacturing reason or some other kind of additional utility. The neck is formed between the ampoule 1 and the collar 22 of the insert body 2. The drawback of having such a neck is that the neck increases the volume within the ampoule 1 and consequently prevents the present invention from achieving minimal holdback space, which occurs following the ejection of a medicated solution through the needle during an injection. In these embodiments, the present invention can be configured with different features in order to reduce the additional volume created by the neck. One such feature is a mechanism that inserts a rigid filler into the neck in order to occupy the additional volume during the injection process. Another such feature is to make the neck out of a collapsible material that folds upon itself near the neck, reducing the internal volume created by said neck feature. Still another feature would be the inclusion of a collapsible section on the ampoule 1 near the neck feature. The collapsible section would fold upon itself reducing the internal volume of the ampoule facilitating a minimal holdback space. In the aforementioned embodiment, the ampoule 1 creates indentations within the neck that would reduce the additional volume.

Referencing FIG. 1, FIG. 2, and FIG. 5-10, the parison layer 12 of the ampoule 1 secures the ampoule 1 to the upper section 20 of the insert body 2. The parison layer is a material layer that engages the upper section 20 through the BFS process. The parison layer 12 of the ampoule 1 is formed during the formation of the prefilled chamber 10 and the flexible body 13. The parison layer initially forms a tubular structure that sleeves the insert body 2. The insert body 2 is oriented into the tubular structure with the upper section 20 directed towards the prefilled chamber 10. It should be noted that the insert body 2 may be particularly weighted to orient the upper section 20 towards the prefilled chamber 10 when used in a gravity fed assembly process. The tubular section would be molded over the upper section 20. The knurl features 21 of the upper section 20 and the knurl features 220 of the collar 22 provide a plurality of ridges that enable the parison layer 12 of the ampoule 1 to effectively engage the collar 22 during the molding process. It should be noted that the parison layer 12 of the ampoule 1 is differentiated from the parison layer 61 of the overtube 6 since the parison layer 12 of the ampoule 1 is retained to the upper section 20 by the knurl features 21 of the upper section 20 and the knurl features 220 of the collar 22. It should be noted that the parison layer 61 of the overtube 6 and the parison layer 12 of the ampoule 1 can be created from the same tubular section during the BFS process.

Referencing FIG. 1-4, the overtube 6 is the protective material that surrounds the insert body 2 and the needle cap 5. The overtube 6 serves as a tamper evident feature as well as a means of preventing the needle cap 5 from compressing the needle assembly 3 into the ampoule 1. The overtube 6 is made from the same material as the ampoule 1 and is molded over the insert body 2 and the needle cap 5 during the BFS process. The overtube 6 comprises a parison layer, a pair of formed tabs 63, and a frangible feature 62. The parison layer 61 of the overtube 6 is molded over the insert body 2 and needle cap 5 while in the initial configuration. Unlike the parison layer 12 of the ampoule 1, the parison layer 61 of the overtube 6 does not engage knurl features that would help retain the parison layer 61 of the overtube 6 to the insert body 2 or the needle cap 5. The lack of retaining features engaging the parison layer 61 of the overtube 6 allows the overtube 6 to be removed from its position. The parison layer 61 of the overtube 6 does reach an adjacent positioning to the parison layer 12 of the ampoule 1. The parison layer 61 of the overtube 6 and the parison layer 12 of the ampoule 1 are separated by the frangible feature 62. The frangible feature 62 separates the parison layer 12 of the ampoule 1 from the parison layer 61 of the overtube 6. The frangible features 62 can be accomplished by scoring or by the thinning of the parison layer. The frangible feature 62 is broke allowing the overtube 6 to remove from the single use injector. The breaking of the frangible feature 62 is facilitated by the use of the pair of formed tabs 63. The pair of formed tabs 63 is laterally positioned on the overtube 6 coincident with the cylindrical wall 23 of the insert body 2. The formed tabs 63 are formed during the BFS process and serves as gripping surfaces for a user's hand. A user is able to rotate the overtube 6 by grasping the laterally positioned formed tabs 63 and rotating the overtube 6 in either a clockwise or counterclockwise rotation. Upon separation of the parison layer 61 of the overtube 6 from the parison layer 12 of the ampoule 1, at the frangible feature 62, the user would pull the overtube 6 away exposing the insert body 2 and the needle cap 5.

In the current embodiment of the present invention, the ampoule 1 and the overtube 6 are constructed from Low Density Polyethylene (LDPE). LDPE is selected as it has several properties favorable to the manufacturing of the single use injector. LDPE can be formulated with particular elastic properties that allow the formation of the flexible body 13 of the ampoule 1. LDPE can be formulated to meet standards of a pharmaceutical grade polymer that include those for sterility as well as being unlikely to react with a medication over an extended period of time. LDPE has favorable melting temperatures that would be optimally suited for the BFS manufacturing process. LDPE additionally has favorable binding properties with Polypropylene (PP).

In the current embodiment of the present invention, the insert body 2, the needle assembly 3, the shield assembly 4, and the needle cap 5 are constructed using polypropylene (PP), with the exception of the needle 35 and the spring 36. PP is a material that is favorable in the construction of the aforementioned components due to it rigid but pliable construction. PP formed components are able to hold their shapes after being formed. Furthermore, PP components have favorable interactions with LPDE components, as LDPE does not fuse to PP components allowing for the separation of an LDPE layer from a PP component.

In the current embodiment of the present invention, the insert body 2, the needle assembly 3, the shield assembly 4, and the needle cap 5 would be assembled into the initial configuration prior to being positioned into a mold with the ampoule 1 and the overtube 6. The insert body 2, the needle assembly 3, and the needle 35 shield have complicated interaction that can require additional attention to ensure that they are properly assembly. By providing the aforementioned components in a pre-assembled state, the BFS aspect of the assembly of the single use injector wouldn't need specialized tools or mechanisms to individually couple each tool.

Although the invention has been explained in relation to its preferred embodiment, it is to be understood that many other possible modifications and variations can be made without departing from the spirit and scope of the invention as hereinafter claimed.

What is claimed is:

1. A single use injector comprises:
an ampoule;
an insert body;
a needle assembly;
a shield assembly;
a needle cap;
an overtube;
the ampoule comprises a prefilled chamber and a first parison layer;
the insert body comprises an upper section, a cylindrical wall, an inner chamber, a first pair of slots and a second pair of slots;
the needle assembly comprises a lateral wall, a cavity, a needle, a spring and a pair of snapping hooks;
the shield assembly comprises activation tabs and a barrel;
the needle cap comprises a rim and a protective cover;
the ampoule, the insert body, the needle assembly, the shield assembly, and the needle cap being centrally aligned;
the needle assembly and the shield assembly being enclosed between the insert body and the needle cap;
the insert body being positioned between the ampoule and the needle cap;
the prefilled chamber being secured against the upper section by the first parison layer;
the needle assembly being moveably aligned within the inner chamber through the cylindrical wall;
the needle assembly being directionally biased towards the upper section of the insert body;
the needle being piercingly aligned with the upper section and the prefilled chamber, wherein the needle is aligned to pierce through the upper section and into the prefilled chamber;
the barrel of the shield assembly being extendably positioned around the needle by way of the spring;
the activation tabs being actuatably engaged to the lateral wall of the needle assembly;
the needle cap being compressibly positioned against the needle assembly by way of the rim;
the needle being encloseably positioned within the protective cover;
the shield assembly being extendably positioned around the needle;
the overtube being removeably positioned surrounding the insert body and the needle cap;
each snapping hook of the pair of snapping hooks comprises a flexible arm and a stud;
the stud being outwardly extended from the flexible arm;
the pair of snapping hooks being oppositely connected to the lateral wall across the cavity;
a corresponding snapping hook among the pair of snapping hooks being accommodated within a corresponding lateral through hole among a pair of lateral through holes of the lateral wall;
each slot of the first pair of slots being positioned across the inner chamber on the cylindrical wall, away from the upper section;
each slot of the second pair of slots being positioned across the inner chamber on the cylindrical wall, adjacent to the upper section;
the first pair of slots being aligned with the second pair of slots towards the upper section;
the pair of snapping hooks being configured to be detachably coupled to the first pair of slots by the stud being detachably engaged with a corresponding slot among the first pair of slots;
the pair of snapping hooks being configured to be detachably coupled to the second pair of slots by the stud being detachably engaged with a corresponding slot among the second pair of slots;
the stud being configured to be compressibly coincident to the cylindrical wall by way of the flexible arm;
the stud and the flexible arm being compressed inwardly towards the cavity in response to the stud moving in between a corresponding slot among the first pair of slots and a corresponding slot among the second pair of slots;
the needle assembly comprises a tapered spring mount;
the shield assembly comprises a spring mount;
the spring mount comprises a needle passage;
the lateral wall comprises needle shield activation channels;
the spring comprises a first spring end and a second spring end;
the activation tabs comprise an elongated arm, a first engagement feature, and a second engagement feature;
each of the needle shield activation channels comprises a first path, a second path and an obstructing feature;
each of the first path and the second path laterally penetrating the lateral wall by being excised from the lateral wall;
the first path and the second path intersecting each other at the obstructing feature with an acute angle;
the needle comprises an injection end;
the second path comprises a locking mount;
the tapered spring mount being centrally positioned within the cavity, wherein the narrow end of the tapered spring mount being oriented towards the shield assembly;
the tapered spring mount traverses the first spring end, wherein the wide end of the tapered spring mount being coincidently positioned with the first spring end;
the second spring end being compressibly retained against the spring mount;
the needle centrally traverses through the tapered spring mount and the needle passage;
the elongated arm being compressibly coupled adjacent the spring mount;
the first engagement feature and the second engagement feature being positioned opposite the spring mount on the flexible arm;
the second engagement feature being actuatably retained in the first path by way of the obstructing feature and the spring;
the second engagement feature being compressibly aligned with the second path by way of the first path;
the first engagement feature being extendably coincident with the locking mount by way of the spring, wherein the first engagement feature securely engages the locking mount; and
the barrel and the spring mount being extendably positioned around the injection end by way of the spring.

2. The single use injector as claimed in claim 1, wherein the pair of snapping hooks being immovably retained to the second pair of slots.

3. The single use injector as claimed in claim 1 comprises:
the insert body comprises a chamber opening and a pair of alignment channels;
the needle assembly comprises a pair of guides and a cavity opening;
the cavity opening being positioned adjacent to the chamber opening;
the pair of alignment channels being recessed into an interior surface of the cylindrical wall adjacent to the cavity opening, wherein the interior surface of the cylindrical wall is the surface coincident with the cavity;
the pair of guides being peripherally positioned on the lateral wall adjacent to the cavity opening, wherein the peripheral positioning places the pair of guides on the exterior surface of the lateral wall;
each guide of the pair of guides being moveably positioned within an alignment channel of the pair of alignment channels, wherein each guide of the pair of guides travels along the length of an alignment channel of the pair of alignment channels; and
the needle assembly being moveably aligned along the length of the pair of alignment channels.

4. The single use injector as claimed in claim 1 comprises:
the upper section of the insert body comprises a collar and knurl features;
the ampoule comprises a flexible body;
the collar comprises knurl features;
the prefilled chamber comprises a medication, an inert gas, and a membrane;
the inert gas and the medication being hermetically sealed within the prefilled chamber;
the prefilled chamber being compressibly surrounded by the flexible body;
the collar being protrudingly positioned on the upper section towards the prefilled chamber, wherein the collar being raised relative to the upper section;
the knurl features of the upper section being perimetrically positioned adjacent to the cylindrical wall, wherein the knurl features revolve the perimeter of the upper section adjacent the cylindrical wall;
the knurl features of the collar being perimetrically positioned around the collar, perpendicular to the upper section;
the flexible body being tapered towards the collar;
the flexible body and the upper section being encasably retained by the first parison layer; and
the first parison layer being moldably coupled to the knurl features of the upper section and the knurl features of the collar.

5. The single use injector as claimed in claim 4 comprises:
the flexible body comprises a first section and a second section;
the first section of the flexible body being symmetrically aligned with the second section of the flexible body enclosing the prefilled chamber;
the first section of the flexible body being tapered towards the collar;
the second section of the flexible body being compressibly coupled to the first section of the flexible body; and
the second section of the flexible body being configured to be compressed into first section of the flexible body for completely expelling the contents of the prefilled chamber.

6. The single use injector as claimed in claim 4 comprises:
the ampoule comprises an adhesive membrane; and
the prefilled chamber being breachably coupled to the collar by way of the adhesive membrane, wherein the prefilled chamber being breachable by the needle through the adhesive membrane.

7. The single use injector as claimed in claim 1 comprises:
the needle assembly comprises a conical shaped needle mount;
the upper section comprises a collar;
the inner chamber comprises a conical shaped cavity;
the collar comprises a guide shaft and a septum;
the needle comprises a puncturing end, an injection end, and a fluid conduit;
the collar being protrudingly positioned on the upper section towards the prefilled chamber, wherein the collar being raised relative to the upper section;
the conical shaped cavity being centrally positioned on the upper section opposite the collar, wherein the conical shaped cavity being coincident with the inner chamber;
the conical shaped needle mount being perpendicularly positioned to the lateral wall adjacent to the conical shaped cavity;
the needle centrally traverses the conical shaped needle mount, wherein the conical shaped needle mount being positioned between the puncturing end and the injection end;
the septum being piercingly aligned to the puncturing end, wherein the puncturing end being aligned to traverse the septum;
the puncturing end being centrally aligned with the guide shaft, wherein the guide shaft being slightly wider in diameter to the puncturing end in order to orient it after piercing the septum;
the conical shaped needle mount being coincidently aligned with the conical shaped cavity, wherein the concavity of the conical shaped cavity being positioned to receive the conical shaped needle mount;
the puncturing end being breachably aligned within the prefilled chamber; and
the injection end being in fluid communication with the prefilled chamber by way of the puncturing end through the fluid conduit.

8. The single use injector as claimed in claim 7 comprises:
the conical shaped needle mount being securely mounted to the conical shaped cavity, wherein the conical shaped needle mount being wider than the conical shaped cavity causing the conical shaped needle mount to wedge into the conical shaped cavity forming a sealed connection.

9. The single use injector as claimed in claim 7 comprises:
the puncturing end of the needle comprises a rounded tip and a conduit opening; and
the rounded tip being terminally positioned on the puncturing end shielding the conduit opening, wherein the rounded tip prevents obstructions of the conduit opening by sheered particles of the septum.

10. The single use injector as claimed in claim 1 comprises:
the overtube comprises a second parison layer, formed tabs, and frangible features;
the needle cap comprises a sleeve mount;
the upper section comprises knurl features;
the knurl features being positioned on the upper section immediately adjacent to the cylindrical wall;
the rim being positioned perpendicular the sleeve mount and the protective cover;

the sleeve mount being moveably positioned around the cylindrical wall, wherein movement of the sleeve mount compresses the rim against the lateral wall;

the second parison layer being removeably positioned top of the insert body and the needle cap;

the formed tabs being laterally positioned on the second parison layer on the overtube; and the frangible features being positioned between the second parison layer and the first parison layer, wherein the frangible features being positioned adjacent to the knurl feature.

11. A single use injector comprises:

an ampoule;

an insert body;

a needle assembly;

a shield assembly;

a needle cap;

an overtube;

the ampoule comprises a prefilled chamber, a flexible body, and a first parison layer;

the insert body comprises an upper section, a cylindrical wall, an inner chamber, a chamber opening, a pair of alignment channels, a first pair of slots and a second pair of slots;

the needle assembly comprises a lateral wall, a cavity, a needle, a spring, a pair of snapping hooks, a pair of guides, a cavity opening, a conical shaped needle mount, and a tapered spring mount;

the shield assembly comprises activation tabs, a barrel, and a spring mount;

the needle cap comprises a rim, a protective cover, and a sleeve mount;

the overtube comprises a second parison layer, formed tabs, and frangible features;

the upper section comprises a collar and knurl features;

the collar comprises knurl features, a guide shaft, and a septum;

the prefilled chamber comprises a medication, an inert gas, and a membrane;

the inner chamber comprises a conical shaped cavity;

the needle comprises a puncturing end, an injection end, and a fluid conduit;

the spring mount comprises a needle passage;

the lateral wall comprises needle shield activation channels;

the spring comprises a first spring end and a second spring end;

the activation tabs comprise an elongated arm, a first engagement feature, and a second engagement feature;

each of the needle shield activation channels comprises a first path, a second path and an obstructing feature;

each of the first path and the second path laterally penetrating the lateral wall by being excised from the lateral wall;

the first path and the second path intersecting each other at the obstructing feature with an acute angle;

the second path comprises a locking mount;

the ampoule, the insert body, the needle assembly, the shield assembly, and the needle cap being centrally aligned;

the needle assembly and the shield assembly being enclosed between the insert body and the needle cap;

the insert body being positioned between the ampoule and the needle cap;

the prefilled chamber being secured against the upper section by the first parison layer;

the needle assembly being moveably aligned within the inner chamber through the cylindrical wall;

the needle assembly being directionally biased towards the upper section of the insert body;

the needle being piercingly aligned with the upper section and the prefilled chamber, wherein the needle is aligned to pierce through the upper section and into the prefilled chamber;

the barrel of the shield assembly being extendably positioned around the needle by way of the spring;

the activation tabs being actuatably engaged to the lateral wall of the needle assembly;

the needle cap being compressibly positioned against the needle assembly by way of the rim;

the needle being encloseably positioned within the protective cover;

the shield assembly being extendably positioned around the needle;

the overtube being removeably positioned surrounding the insert body and the needle cap;

each snapping hook of the pair of snapping hooks comprises a flexible arm and a stud;

the stud being outwardly extended from the flexible arm;

the pair of snapping hooks being oppositely connected to the lateral wall across the cavity;

a corresponding snapping hook among the pair of snapping hooks being accommodated within a corresponding lateral through hole among a pair of lateral through holes of the lateral wall;

each slot of the first pair of slots being positioned across the inner chamber on the cylindrical wall, away from the upper section;

each slot of the second pair of slots being positioned across the inner chamber on the cylindrical wall, adjacent to the upper section;

the first pair of slots being aligned with the second pair of slots towards the upper section;

the pair of snapping hooks being configured to be detachably coupled to the first pair of slots by the stud being detachably engaged with a corresponding slot among the first pair of slots;

the pair of snapping hooks being configured to be detachably coupled to the second pair of slots by the stud being detachably engaged with a corresponding slot among the second pair of slots;

the stud being configured to be compressibly coincident to the cylindrical wall by way of the flexible arm;

the stud and the flexible arm being compressed inwardly towards the cavity in response to the stud moving in between a corresponding among the first pair of slots and a corresponding slot among the second pair of slots;

the cavity opening being positioned adjacent to the chamber opening;

the pair of alignment channels being recessed into an interior surface of the cylindrical wall adjacent to the cavity opening, wherein the interior surface of the cylindrical wall is the surface coincident with the cavity;

the pair of guides being peripherally positioned on the lateral wall adjacent to the cavity opening, wherein the peripheral positioning places the pair of guides on the exterior surface of the lateral wall;

each guide of the pair of guides being moveably positioned within an alignment channel of the pair of alignment channels, wherein each guide of the pair of guides travels along the length of an alignment channel of the pair of alignment channels;

the needle assembly being moveably aligned along the length of the pair of alignment channels;

the inert gas and the medication being hermetically sealed within the prefilled chamber;

the prefilled chamber being compressibly surrounded by the flexible body;

the collar being protrudingly positioned on the upper section towards the prefilled chamber, wherein the collar being raised relative to the upper section;

the knurl features of the upper section being perimetrically positioned adjacent to the cylindrical wall, wherein the knurl features revolve the perimeter of the upper section adjacent the cylindrical wall;

the knurl features of the collar being perimetrically positioned around the collar, perpendicular to the upper section;

the flexible body being tapered towards the collar;

the flexible body and the upper section being encasably retained by the first parison layer;

the first parison layer being moldably coupled to the knurl features of the upper section and the knurl features of the collar;

the collar being protrudingly positioned on the upper section towards the prefilled chamber, wherein the collar being raised relative to the upper section;

the conical shaped cavity being centrally positioned on the upper section opposite the collar, wherein the conical shaped cavity being coincident with the inner chamber;

the conical shaped needle mount being perpendicularly positioned to the lateral wall adjacent to the conical shaped cavity;

the needle centrally traverses the conical shaped needle mount, wherein the conical shaped needle mount being positioned between the puncturing end and the injection end;

the septum being piercingly aligned to the puncturing end, wherein the puncturing end being aligned to traverse the septum;

the puncturing end being centrally aligned with the guide shaft, wherein the guide shaft being slightly wider in diameter to the puncturing end in order to orient it after piercing the septum;

the conical shaped needle mount being coincidently aligned with the conical shaped cavity, wherein the concavity of the conical shaped cavity being positioned to receive the conical shaped needle mount;

the puncturing end being breachably aligned within the prefilled chamber;

the injection end being in fluid communication with the prefilled chamber by way of the puncturing end through the fluid conduit;

the tapered spring mount being centrally positioned within the cavity, wherein the narrow end of the tapered spring mount being oriented towards the shield assembly;

the tapered spring mount traverses the first spring end, wherein the wide end of the tapered spring mount being coincidently positioned with the first spring end;

the second spring end being compressibly retained against the spring mount;

the needle centrally traverses through the tapered spring mount and the needle passage;

the elongated arm being compressibly coupled adjacent the spring mount;

the first engagement feature and the second engagement feature being positioned opposite the spring mount on the flexible arm;

the second engagement feature being actuatably retained in the first path by way of the obstructing feature and the spring;

the second engagement feature being compressibly aligned with the second path by way of the first path;

the first engagement feature being extendably coincident with the locking mount by way of the spring, wherein the first engagement feature is-securely engages the locking mount;

the barrel and the spring mount being extendably positioned around the injection end by way of the spring;

the knurl features being positioned on the upper section immediately adjacent to the cylindrical wall;

the rim being positioned perpendicular the sleeve mount and the protective cover;

the sleeve mount being moveably positioned around the cylindrical wall, wherein movement of the sleeve mount compresses the rim against the lateral wall;

the second parison layer being removeably positioned top of the insert body and the needle cap;

the formed tabs being laterally positioned on the second parison layer on the overtube; and the frangible features being positioned between the second parison layer and the first parison layer, wherein the frangible features being positioned adjacent to the knurl feature.

12. The single use injector as claimed in claim 11, wherein the pair of snapping hooks being immovably retained to the second pair of slots.

13. The single use injector as claimed in claim 11 comprises:

the flexible body comprises a first section and a second section;

the first section of the flexible body being symmetrically aligned with the second section of the flexible body enclosing the prefilled chamber;

the first section of the flexible body being tapered towards the collar;

the second section of the flexible body being compressibly coupled to the first section of the flexible body; and the second section of the flexible body being configured to be compressed into first section of the flexible body for completely expelling the contents of the prefilled chamber.

14. The single use injector as claimed in claim 11 comprises:

the ampoule comprises an adhesive membrane; and the prefilled chamber being breachably coupled to the collar by way of the adhesive membrane, wherein the prefilled chamber being breachable by the needle through the adhesive membrane.

15. The single use injector as claimed in claim 11 comprises:

the conical shaped needle mount being securely mounted to the conical shaped cavity, wherein the conical shaped needle mount being wider than the conical shaped cavity causing the conical shaped needle mount to wedge into the conical shaped cavity forming a sealed connection.

16. The single use injector as claimed in claim 11 comprises:

the puncturing end of the needle comprises a rounded tip and a conduit opening; and the rounded tip being terminally positioned on the puncturing end shielding the conduit opening, wherein the rounded tip prevents obstructions of the conduit opening by sheered particles of the septum.

\* \* \* \* \*